United States Patent [19]

Saulnier

[11] Patent Number: 4,916,217
[45] Date of Patent: Apr. 10, 1990

[54] PHOSPHORUS CONTAINING DERIVATIVES OF EPIPODOPHYLLOTOXIN

[75] Inventor: Mark G. Saulnier, Middletown, Conn.

[73] Assignee: Bristol-Myers Company, New York, N.Y.

[21] Appl. No.: 1,281

[22] Filed: Jan. 8, 1987

[51] Int. Cl.$^4$ .................... C07H 15/00; C07H 17/00
[52] U.S. Cl. .................................... 536/17.1; 536/4.1; 536/18.1; 536/117
[58] Field of Search ............... 536/18.1, 17.1, 1, 117, 536/4.1; 514/27, 34

[56] References Cited

U.S. PATENT DOCUMENTS

| 3,188,309 | 6/1965 | Mukaiyama et al. | 536/17.1 |
| 3,408,441 | 10/1968 | Wartburg et al. | 536/18.1 |
| 3,524,844 | 8/1970 | Keller-Juslen et al. | 536/18.1 |
| 3,558,595 | 1/1971 | Jones et al. | 536/17.1 |
| 4,481,196 | 11/1984 | Teraji et al. | 536/55.3 |
| 4,515,783 | 5/1985 | Linn et al. | 536/18.1 |
| 4,547,567 | 10/1985 | Umezawa et al. | 536/18.1 |
| 4,564,675 | 1/1986 | Kurabayashi et al. | 536/18.1 |
| 4,609,644 | 9/1986 | Nemec | 536/18.1 |
| 4,757,138 | 7/1988 | Fujii et al. | 536/18.1 |

FOREIGN PATENT DOCUMENTS

| 2832009 | 1/1980 | Fed. Rep. of Germany | 514/34 |
| 2033393 | 5/1980 | United Kingdom | 514/34 |

Primary Examiner—Ronald W. Griffin
Assistant Examiner—Nancy S. Carson
Attorney, Agent, or Firm—Robert E. Carnahan; Mollie M. Yang

[57] ABSTRACT

Etoposide-3',4'-quinone is converted into a phosphorane or phosphate ester by reaction with an organic phosphine or phosphite. The resulting phosphoranes and phosphates have anti-tumor activity in animals.

10 Claims, No Drawings

PHOSPHORUS CONTAINING DERIVATIVES OF EPIPODOPHYLLOTOXIN

BACKGROUND OF THE INVENTION

1. Field of the Invention

The present invention provides phosphorous containing derivatives of epipodophyllotoxin glucoside aldehyde or ketone condensation products which have the ability to inhibit transplanted tumors in experimental animals and to the therapeutic anti-tumor use and pharmaceutical dosage forms of these new agents.

2. Description of the Prior Art

Etoposide (VP-16, Ia) and teniposide (VM-26, II) are clinically useful anticancer agents derived from the naturally occurring lignan, podophyllotoxin (III). The numbering system used for nomenclature purposes is shown in Formula III. Note that podophyllotoxin and etoposide, an epipodophyllotoxin derivative, are epimeric at the 4-position. Etoposide and teniposide are active in the treatment of a variety of cancers including small cell lung cancer, non-lymphocytic leukemia, and nonseminomatous testicular cancer (AMA Drug Evaluations, 5th Edition, American Medical Association, 1983, Chicago, Ill. p. 1554–1555).

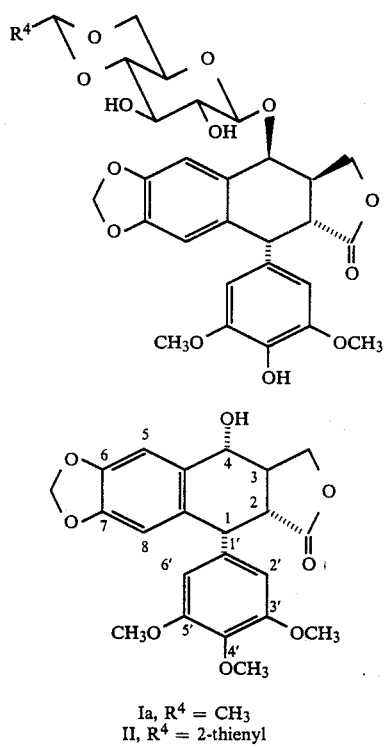

Ia, $R^4$ = $CH_3$
II, $R^4$ = 2-thienyl

Etoposide and teniposide, and methods for producing them, are disclosed in U.S. Pat. No. 3,524,844 to Keller-Juslen et al. which similarly discloses a series of compounds having Formula I wherein $R^4$ has the broader definition given below with respect to Formula V. Etoposide-3', 4'-quinone Formula IV, is derived from etoposide by oxidation as described by Josef Nemec in U.S. Pat. No. 4,609,644, patented Sept. 2, 1986. The quinone IVa has been implicated as a reactive intermediate in the metabolic activation of etoposide by rat liver and hela microsomal fractions (Van Maanen, J. M.; Holthuis, J. J.; Gobas, F. et al. Proc. Am Assoc. Cancer Res. 1983, 24, 319), and also has been suggested as a bioalkylating agent in a report describing the metabolism of etoposide by mouse liver microsomes (see Haim, N.; Nemec, J.; Roman, J.; Sinha, B. K. presented at the American Society for Pharmacology and Experimental Therapeutics meetings at Boston, Mass., Aug. 18–22, 1985). Etoposide-3', 4'-quinone has been generated from electrochemical oxidation of etoposide (see Holthuis, J. J.; Van Oort, W. J.; Romkens, F.M.G.M.; Renema, J. J. J. Electroanal. Chem. 1985, 1984, 317).

Etoposide-3', 4'-quinone IVa serves as the starting material for our preparation of the etoposide phosphorous derivatives of the present invention.

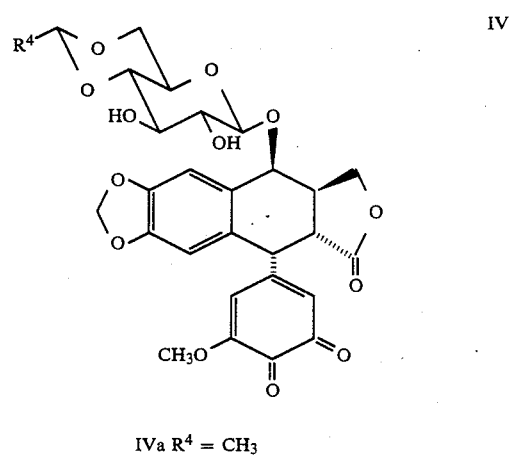

IVa $R^4$ = $CH_3$

α-Diketones such as butane-2,3-dione, benzil, and ortho-quinones such as 9,10-phenanthraquinone are known to react with trialkyl-and triarylphosphites of the formula $(RO)_3P$ to yield cyclic oxyphosphoranes (F. Ramirez and N. B. Desai, J. Amer. Chem. Soc. 82, 2652 (1960)). More recently the reaction has been applied to a more complex ortho-quinone derived from pyrrolo(3,2-e)indole (Magnus et al., J. Chem. Soc., Chem. Commun. 1162–1164 (1986)).

Phosphines in which the phosphorous atom is part of a strained cyclic structure such as 1-phenyl-2,2,4,4-tetramethylphosphetidine react with highly reactive ketones such as hexafluoroacetone to yield bicyclic oxyphosphoranes (L. D. Quin, "The Heterocyclic Chemistry of Phosphorous" John Wiley and Sons, New York 1981 pp. 168–170).

SUMMARY OF THE INVENTION

The present invention is concerned with epipodophyllotoxin derivatives of Formula V wherein $R^4$ and $R^5$ represent the carbonyl attached groups of an aldehyde or ketone of the formula $R^4R^5CO$ which is capable of condensing with epipodophyllotoxin glucoside as described in the Keller-Juslen patent cited above, U.S. Pat. No. 3,524,844. $R^6$ has one of Formulas Va, Vb, or Vc, or Vd.

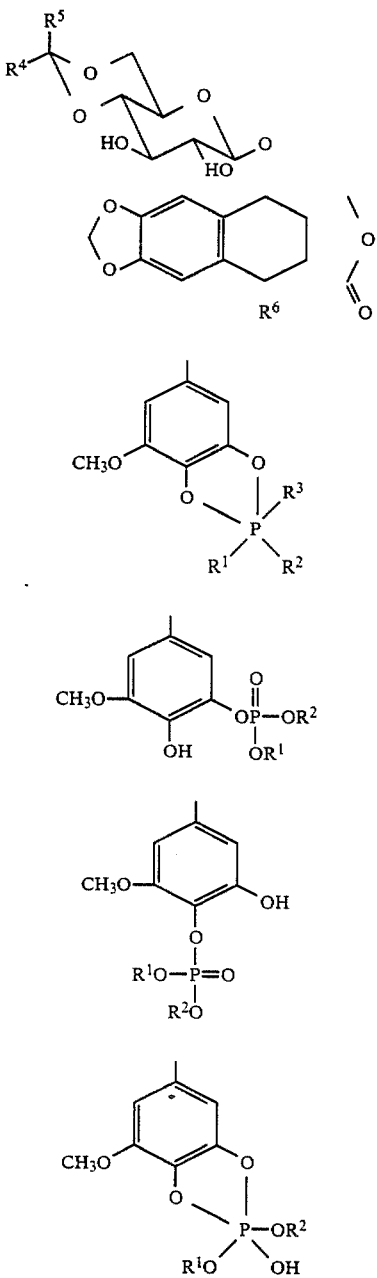

R¹, R², and R³ are substituted or unsubstituted organic groups having a maximum of 20 carbon atoms and independently selected from the group consisting of alkyl or A-substituted alkyl having 1–12 carbon atoms, alkenyl or A-substituted alkenyl having 2–12 carbon atoms, cycloalkyl or A-substituted cycloalkyl having 3–7 ring carbon atoms, aryl or B-substituted aryl having 6–10 ring carbon atoms, aralkyl or B-substituted aralkyl having 6–10 ring carbon atoms, and 1–4 carbon atoms in the alkyl portion, and heteroaryl, B-substituted heteroaryl, heteroaralky or B-substituted heteroalkyl having 4–8 ring members at least one of which is carbon and 1–4 of which are heteroatoms selected from O, N, or S, wherein said A substituents are one or more groups selected from hydroxy, alkoxy, alkanoyloxy, cyano, amino, alkylamino, dialkylamino, carboxy, alkylthio, mercapto, alkanoylamino, alkanoyl, carbamoyl, and halo, and said B substituents are selected from alkyl or a group listed in the A substituent definition, and $R^4$ and $R^5$ are each an alkyl group having 1–10 carbon atoms, or they are joined to form with the carbon atom to which they are attached a cycloalkyl group of 5 or 6 ring members, or one of them is hydrogen and the other is $C_{1-10}$ alkyl, $C_{2-10}$ alkenyl, $C_{4-7}$ cycloalkyl, furyl, thienyl, $C_{6-10}$ aryl, or $C_{7-14}$ aralkyl and said aryl or aralkyl ring optionally bears one or more B substituents as defined above.

The compounds of the present invention are antitumor agents whose utility has been demonstrated against transplanted tumors in experimental animals, for instance P388 murine leukemia. They also exhibit tumor inhibitory activity in vitro against various mammalian tumors, including human tumors grown in tissue culture. In the treatment of mice inoculated with P388 ascites fluid according to the validated experimental protocol described below, they have exhibited lower toxicity than etoposide as reflected by the lack of weight loss of the treated animals.

In view of the antitumor activity observed in experimental animal tumors, and the relatively low toxicity of the claimed compounds, the invention includes use of the substances for inhibiting mammalian tumors. For this purpose they are administered systematically to a mammal bearing a tumor in substantially non-toxic antitumor effective dose. Oral or parenteral administration is intended.

They are administered by injection in much the same way and for some of the same purposes as etoposide or teniposide. Somewhat larger or smaller doses may be employed depending upon the particular tumor sensitivity. They are readily distributed as dry pharmaceutical compositions containing diluents, buffers, stabilizers, solubilizers, and ingredients contributing to pharmaceutical elegance. These compositions are then constituted with an injectable liquid medium extemporaneously just prior to use. Suitable injectable liquids include water, isotonic saline, etc. for oral use, soft gelatin capsules having a liquid fill composition containing the active ingredient, or hard gelatin capsules containing a dry pulverulent composition may be used. Tablets containing appropriate carriers and lubricants, etc. may be prepared in conventional fashion.

Etoposide-3',4'-quinone and the congeneric 3',4'-quinones of Formula IV readily react with phosphines and phosphites of Formulas VI and VII in which $R^1$, $R^2$, and $R^3$ have the same meanings previously given with respect to Formula V to yield the products of the present invention.

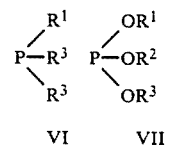

VI     VII

DETAILED DESCRIPTION OF THE INVENTION

The preparative reaction of the present invention takes place readily in solution in a reaction inert organic solvent. Contact of the reactants for only a few minutes seems to be sufficient for completion of the reaction. Suitable solvents are methylene chloride and others. A reaction period of 16 hours is frequently employed, but 1 to 2 hours is usually sufficient, and on a small bench top scale 10 minutes may be sufficient. An excess of the phosphine or phosphite reactant is used to ensure efficient consumption of the more expensive 3'4'-quinone reactant of Formula IV. The stoichiometry of the reaction requires equimolar amounts of phosphine or phosphite and 3'4'-quinone IV, but use of from 10 to 50 mole % excess of the phosphine or phosphite VI is recommended.

Completion of the reaction may be determined visually because the 3'4'-quinone reactant is deep-red in color, and the color disappears as the 3',4'-quinone is consumed. Thin layer chromatography (TLC) is also convenient for monitoring completion of the reaction.

The product is recovered and purified by evaporation of the reaction solvent, and crystallization of the residue or application of chromatography thereto. The purified material may then be recrystallized from appropriate solvents to achieve further purification. Aqueous acidic conditions are to be avoided because of the presence of hydrolyzable bonds in the glucosidic product structure.

In the case of the phosphine reactants of Formula VI the products are cyclic oxyphosphoranes of Formula Va. In the case of phosphite reactants of Formula VII, the products are mixtures of phosphate esters of Formulas Vb and Vc. Generally the phosphate ester mixtures may be used without separation for the antitumor purposes of the present invention. If separation is desired, means used by those skilled in the art are available.

It is believed that the cyclic pentacovalent phosphate species of Formula V wherein $R^6$ has Formula Vd, enjoys an existence in solutions of the esters of Formulas Vb and Vc.

The 146 MHz $^{31}P$ nuclear magnetic resonance spectrum in CDCl$_3$ displayed by the mixture of phosphates Vb and Vc exhibits two major signals of equal intensity at $\delta -4.8$ ppm and $-6.9$ ppm in addition to a small peak at $-2.9$ ppm. This minor peak is believed to be due to the pentacovalent phosphorous species Vd in equilibrium with Vb and Vc. This type of equilibration has been suggested by P. Magnus et al J. Chem. Soc., Chem. Common, 1986, 1162 to explain an alkylative rearrangement of a related ortho-phenolic phosphate ester. Our data lends support to the existence of a pentacovalent phosphorous species Vd.

Antitumor Activity

The results of antitumor evaluation of the compounds of the examples are summarized in the tables which follow. The test data involves a cytotoxicity assay versus various murine and human tumors, and in vivo evaluation against P-388 leukemia and B16 melanoma in mice.

Cytotoxicity Assay

The in vitro cytotoxicity assay involved growing various mammalian tumor cells, including human tumor cells, on microtitre plates employing established tissue culture methods. The concentration of each compound required to inhibit cell growth by 50% (IC$_{50}$) was then determined by a four-fold serial dilution technique. The validity of the method has been supported by a report published in the "Proceedings of the American Association for Cancer Research", Vol. 25, 328, p. 1891 (1984). Tumor cells of the following types were employed for each compound tested: B16-F10 murine melanoma; Moser human colon; M109 murine lung; and three human colon tumor cell lines namely HCT-116, HCT-VM, and HCT-VP, the latter two being resistant to teniposide (VM) and etoposide (VP). A wide range of IC$_{50}$ values was observed, and quantitative comparisons amongst test compounds or against the etoposide control values were not possible. The lowest IC$_{50}$ value, 13.1 mcg/ml, was observed with the compound of Example 4 against the B16-F10 murine melanoma. In that system etoposide exhibited IC$_{50}$ values in the range of 9–12 mcg/ml. The four exemplified compounds were shown to be active (IC$_{50} <$ 500 mcg/ml) against each of the tumors.

TABLE I

Cytotoxicity Assay
IC$_{50}$ (mcg/ml) Value of Compounds of Numbered Examples*

| No. | B16-F10 | HCT-116 | HCT/VM | HCT/VP | Moser | M109 |
|---|---|---|---|---|---|---|
| 1 | 23(9.2) | 47(21.6) | 56(39) | 108(124) | 64(139) | |
|   | 47(27) | 46(19) | 45(30) | 89(95) | 85(148) | |
| 2 | 21(2.7) | 9.8(2.1) | 23(6.1) | 74(30) | 74(38) | 76(67) |
|   | 30(1.9) | 10.6(2.7) | 55(3.1) | 80(41) | 70(39) | 71(12.5) |
| 3 | 20(2.7) | 15.6(2.1) | 35(6.1) | 64(30) | 105(38) | 54(67) |
|   | 22(1.9) | 14.3(2.7) | 56(3.1) | 99(41) | 79(39) | 56(12.5) |
| 4 | 20.7(12.1) | 83(9.5) | 63(126) | 203(195) | 84(226) | >125(53) |
|   | 13.1(9.1) | 39(40) | 82(46) | 168 (>500) | | 97(53) |

*The values shown in parentheses are for etoposide in the same run. Values <500 mcg/ml are a positive indicator of activity; quantitative comparisons are not intended.

P-388 Murine Leukemia

The test protocol involved CDF$_1$ female mice implanted intraperitoneally with a tumor inoculum of 10$^6$ ascites cells of P-388 murine leukemia and treated with various doses of a test compound, or with etoposide. The compounds were administered by intraperitoneal injection on various schedules. Groups of four mice were used for each dosage schedule and amount. A group of ten saline treated control mice was included in each series of experiments, and etoposide treated groups of six were included as a positive control. Thirty one, 47, and 49 day protocols were employed with the mean survival time in days being determined for each group of mice and the number of survivors at the end of the period being noted. The mice were weighed before treatment and again on day 5 or day 6. Mice weighing 20 grams each were employed and a loss in weight of up to approximately 2 grams was not considered excessive. The results are arranged in Table II and were determined in terms of % T/C which is the ratio of the mean survival time of the treated group to the mean survival time of the saline treated control group times 100. The saline treated control animals usually died within nine days. The "maximum effect" in the table is expressed as % T/C and the dose giving that effect is reported. Two different dosage regimens were employed. In one, the first dose of test drug was given on Day 1, the day of tumor inoculation, and second was given on Day 5. In the other, the first dose of test drug was given on Day 5 and a second dose on Day 8. According to the latter protocol, the etoposide control % T/C values are lower than according to the former protocol indicating a more stringent test regimen. Greater effectiveness for the compounds of Examples 2 and 3 is reflected by the higher % T/C values relative to etoposide.

TABLE II

| | In Vivo Antitumor Activity Murine leukemia P-388 | | | |
|---|---|---|---|---|
| | Maximum Effect | | | Average |
| Compound (Example No.) | Dose (mg/kg) | % T/C | Treatment Days | Weight Change |
| 1 | 120 | >544 | 1, and 5 | −0.7 |
| 4 | 120 | 150 | 1, and 5 | +0.2 |
| Etoposide | 40 | >450 | 1, and 5 | −1.9 |
| | 60 | >573 | 1, and 5 | −0.4 |
| 2 | 160 | 305 | 5, and 8 | +2.6 |
| 3 | 200 | 285 | 5, and 8 | +3.2 |
| Etoposide | 60 | 280 | 5, and 8 | +2.1 |

B16 Melanoma

The compound of Example 1 was shown to be active against the B16 melanoma implanted subcutaneously into $BDF_1$, female mice as reflected by the prolongation of survival in a protocol of the sort described above with respect to P388 leukemia. Using intraperitoneal dosage, a dose of 40 mg/kg of body weight afforded % T/C of 145%. Etoposide showed % T/C of >177 at 100 mg/kg.

DESCRIPTION OF SPECIFIC EMBODIMENTS

Melting points were determined in a capillary melting point apparatus and are uncorrected. Proton and carbon nuclear magnetic resonance (NMR) spectra (using $CDCl_3$ as an internal reference) and phosphorous NMR spectra (using 85% aqueous $H_3PO_4$ as an external reference) were recorded on a Bruker WM360 spectrometer. Infrared spectra (IR) were determined on a Perkin-Elmer 1800 Fourier Transform Infrared Spectrophotometer and ultraviolet spectra (UV) were recorded using a Hewlett-Packard 8450 ultraviolet/visible spectrophotometer. "Flash chromotography" refers to the method described by Still (Still, W. C.; Kahn, M.; Mitra, A. J. Org. Chem. 1978, 43, 2923) and was carried out using E. Merck silica gel (230–400 mesh).

EXAMPLE 1

ETOPOSIDE-3',4'-DIOXATRIETHYLPHOSPHORANE

A solution of etoposide-3',4'-quinone, IVa 185 mg (0.323 mmol), in $CH_2Cl_2$ (8 ml) is treated dropwise over 0.5 min. with triethylphosphine (58 μl, 0.39 mmol) neat via syringe with stirring. After 10 min. the solvent is evaporated in vacuo and the product is purified by flash chromatography on silica gel using 5% $CH_3OH$ in $CH_2Cl_2$ to give 185 mg (83%) of the title compound as a colorless solid, mp 164°-167° C.

IR(KBr) 3440, 3375, 1775, 1636, 1577, 1485, 1306, 1271, 1235, 1116, 1095, 1076, 1039, 1001, 935, 890, 877, 785, 764, 734, cm−1.

UV ($CH_3OH$)λmax (log ε) 286 (3.622), 291 (3.617)nm. 360 MHz$^1$H NMR ($CDCl_3$)δ6.79 (s,1H), 6.57 (d,1H), 6.49 (s,1H), 5.93(m,2H) 5.78 (d,1H), 4.87 (d,1H), 4.71 (q,1H), 4.56 (d,1H), 4.49 (d,1H), 4.39 (dd,1H), 4.19–4.12 (m,2H), 3.82 (s,3H), 3.67 (dd,1H), 3.55 (dd,1H), 3.41 (m,1H), 3.33–3.22 (m,3H), 2.94–2.88 (m,1H), 1.73–1.62 (m,6H), 1.37(d,3H), 1.18–1.05 (m,9H).

90 MHz$^{13}$C NMR ($CDCl_3$/DMSO-d6)δ1.74.8, 148.2, 146.9, 146.4, 143.7, 1.33.1, 132.1, 130.6, 127.6, 110.5, 110.3, 109.2, 106.5, 101.0, 100.9, 99.2, 79.5, 74.5, 73.1, 72.5, 67.8, 67.5, 65.9, 55.9, 43.2, 40.7, 37.2, 20.0, 19.5, 18.8, 5.2.

146 MHz $^{31}$P NMR ($CDCl_3$/DMSO-d6)δ57.4.

EXAMPLE 2

Etoposide-3',4'-Dioxa-(Bis-(Hydroxymethyl)Methylphosphorane

To a solution of etoposide-3',4'-quinone (IVa), 216 mg. (0.378 mmol), in $CH_2Cl_2$ (20 ml) there is slowly added during 1-2 min. a solution of bis-(hydroxymethyl)methylphosphine, 53.5 mg., (0.495 mmol) in $CH_2Cl_2$ (2 ml) with stirring. The mixture is stirred at room temperature for 1.5 hours and the solvent is evaporated in vacuo. The product is purified by flash chromatography on silica gel using 5% $CH_3OH$ in $CH_2Cl_2$ to provide 113 mg (44%) of the title compound as a white solid, mp 212°-214° C.

IR (KBr) 3425, 1773, 1625, 1510, 1490, 1335, 1235, 1160, 1095, 1080, 1040, 1005, 935, 875, 770, 700 cm−1.

360 MHz $^1$H NMR ($CDCl_3$/DMSO-d6)δ6.74 (s,1H), 6.45 (d,1H,J=1.9 Hz), 6.42 (s,1H), 5.87 (m,2H), 5.75 (d,1H,J=1.9 Hz), 4.83 (d,1H,J=3.4 Hz), 4.67 (q,1H,J=5.0 Hz),4.46–4.33 (m,3H), 4.20–3.83 (m,6H), 3.74 (s,3H), 3.57–3.47 (m,2H), 3.33–3.21 (m,4H), 2.87–2.82 (m,1H), 1.30 (d,3H,J=5.0 Hz), 1.11 (d,3H,J=2.9 Hz).

90 MHz$^{13}$C NMR ($CDCl_3$/DMSO-d6)δ175.0, 148.3, 146.8, 146.6, 143.7, 133.2, 132.0, 130.8, 127.6, 110.5, 110.4, 109.2, 106.6, 101.1, 100.9, 99.4, 79.6, 74.5, 73.2, 72.6, 67.9, 67.6, 66.0, 62.0 (d,$J_{CP}$=18.1 Hz), 56.0, 43.4, 40.8, 37.2, 20.1, 1.45 (d,$J_{CP}$=11 HZ).

146 MHz$^{31}$P NMR ($CDCl_3$/DMSO-d6)δ −37.5

EXAMPLE 3

Etoposide-3',4'-Dioxa-Tris-(2-Cyanoethyl)Phosphorane

To a solution of etoposide-3,4'-quinone, 248 mg. (0.433 mmol), in $CH_2Cl_2$ (22 ml) there is slowly added during 15 min. with stirring a solution of tris-(2-cyanoethyl)phosphine, 86.9 mg. (0.450 mmol), in $CH_2Cl_2$ (10 ml). The resulting light yellow mixture is stored at 0° C. for 1.5 h. and then filtered to give 135 mg of a light yellow solid. The formation of the desired product containing a small amount of the starting quinone is shown by TLC. Concentration of the filtrate and further drying at 0.1 torr provided 225 mg (68%) of the pure title compound as a white solid, mp 168°-172° C. (decomp at 190° C.).

IR (KBr) 3445, 2255, 1773, 1620, 1488, 1338, 1237, 1095, 1080, 1040, 1005, 935, 890, 870, 775, 700 cm−1.

360 MHz $^1$H NMR ($CDCl_3$)δ6.69 (s,1H), 6.35 (s,1H), 6.33 (d,1H,J=1, 7 Hz), 5.80 (m,2H), 5.73 (d,1H,J=1.7 Hz), 4.78 (d,1H,J=3.3 Hz), 4.60 (q,1H,J=5.0 Hz), 4.39–4.27 (m,3H), 4.08–4.01 (m,2H), 3.66 (s,3H), 3.48–3.43 (m,2H), 3.27–3.13 (m,4H), 2.80–2.12 (m,13H), 1.23 (d,3H,J=5.0 Hz).

EXAMPLE 4

Etoposide-Bis-(2-Chloroethyl)Phosphate, Mixture of 3' and 4'Regioisomers

A solution of the etoposide-3',4'-quinone (IV), 185.7 mg., 0.3246 mmol, in $CH_2Cl_2$ (10 ml) is treated dropwise while stirring with tris-(2-chloroethyl)phosphite (90 μL, 0.44 mmol) neat via syringe during one minute. The mixture is stirred at room temperature for 16 h, concentrated under a stream of $N_2$ to ca 2 ml, and flash chromatographed on silica gel using 5% $CH_3OH$ in $CH_2Cl_2$. The product is obtained as an off-white solid, 239 mg, (94.5%). The $^1$H and $^{31}$P NMR spectra clearly indicated a 1:1 mixture of regioisomeric phosphates.

IR (KBr) 3430, 1775, 1625, 1610, 1515, 1495, 1240, 1085, 1040, 875, 705, cm−1.

Partial 360 MHz $^1$H NMR (CDCl$_3$)δ7.70 (s,1H,phenol OH), 6.85 and 6.77 (d's 1H, 6'H of each isomer), 6.80 and 6.78 (s's, 1H, 5H of each isomer), 6.50 and 6.49 (s's, 1H,8H of each isomer), 6.13 and 5.78 (d's, 1H, 2'H of each isomer), 6.02 (s,1H, phenol OH), 3.83, 3.82 (s's, 3H, OCH$_3$ of each isomer).

146 MHz $^{31}$P NMR (CDCl$_3$)δ−4.8, −6.9.

EXAMPLE 5

The phosphines listed below are substituted in Examples 1, 2, or 3 for the phosphines identified in those examples. Products of Formula Va are produced and isolated in a fashion similar to that described in the examples.

| PRODUCTS OF EXAMPLE 5 | | |
|---|---|---|
| Phospine Reactant | Product of Formula Va | |
| N,N-bis (Diphenylphophino)aniline | $R^1$ | $C_6H_5$— |
| | $R^2$ | $C_6H_5$— |
| | $R^3$ | —N— |
| | | \|  |
| | | $C_6H_5$ |
| 1,4-bis(Diphenylphosphino)butane | $R^1$ | $C_6H_5$— |
| | $R^2$ | $C_6H_5$— |
| | $R^3$ | *—CH$_2$CH$_2$CH$_2$CH$_2$— |
| (−)-(2S,3S)-bis(Diphenylphosphino)-butane | $R^1$ | $C_6H_5$— |
| | $R^2$ | $C_6H_5$— |
| | $R^3$ | *CH$_3$CHCHCH$_3$ |
| bis-(Diphenylphosphino)methane | $R^1$ | $C_6H_5$— |
| | $R^2$ | $C_6H_5$— |
| | $R^3$ | *—CH$_2$— |
| 1,3-bis-(Diphenylphosphino)propane | $R^1$ | $C_6H_5$— |
| | $R^2$ | $C_6H_5$— |
| | $R^3$ | *—CH$_2$CH$_2$CH$_2$— |
| Butyldiphenylphosphine | $R^1$ | $C_6H_5$— |
| | $R^2$ | $C_6H_5$— |
| | $R^3$ | n-C$_4$H$_9$— |
| Chlorodiphenylphosphine | $R^1$ | $C_6H_5$— |
| | $R^2$ | $C_6H_5$— |
| | $R^3$ | Cl |
| Dichlorophenylphosphine | $R^1$ | Cl— |
| | $R^2$ | Cl— |
| | $R^3$ | $C_6H_5$— |
| Dicyclohexylphosphine | $R^1$ | cyclohexyl |
| | $R^2$ | cyclohexyl |
| | $R^3$ | H |
| Dimethylphenylphosphine | $R^1$ | CH$_3$— |
| | $R^2$ | CH$_3$— |
| | $R^3$ | $C_6H_5$— |
| Methyldiphenylphosphine | $R^1$ | CH$_3$— |
| | $R^2$ | $C_6H_5$— |
| | $R^3$ | $C_6H_5$— |
| Tributylphosphine | $R^1$ | n-C$_4$H$_9$— |
| | $R^2$ | n-C$_4$H$_9$— |
| | $R^3$ | n-C$_4$H$_9$— |
| Tricyclohexylphosphine | $R^1$ | cyclohexyl |
| | $R^2$ | cyclohexyl |
| | $R^3$ | cyclohexyl |

*bis products having two nuclei of Formula Va joined at phosphorous through the bridging group shown as $R^3$.

EXAMPLE 6

The following organic phosphites are substituted in Example 4 for tris-(2-chloroethyl)phosphite to produce mixtures of Formulas Vb, and Vc, wherein $R^4$ is hydrogen, $R^5$ is methyl, and $R^1$, $R^2$ and $R^3$ have the values shown in the table.

| PRODUCTS OF EXAMPLE 6 | | | | |
|---|---|---|---|---|
| Phosphite Reactant | Products of Formulas Vb and Vc | | | |
| Benzyldiethylphosphite | $R^1$ | ethyl | $R^1$ | ethyl |
| | $R^2$ | ethyl | $R^2$ | benzyl |
| | $R^1$ | ethyl | $R^1$ | ethyl |
| | $R^2$ | benzyl | $R^2$ | ethyl |
| Ethyldichlorophosphite | $R^1$ | chloro | $R^1$ | ethyl |
| | $R^2$ | chloro | $R^2$ | chloro |
| | $R^1$ | ethyl | $R^1$ | chloro |
| | $R^2$ | chloro | $R^2$ | chloro |
| Methyldichlorophosphite | $R^1$ | chloro | $R^1$ | methyl |
| | $R^2$ | chloro | $R^2$ | chloro |
| | $R^1$ | methyl | $R^1$ | chloro |
| | $R^2$ | chloro | $R^2$ | chloro |
| Tributylphosphite | $R^1$ | n-Bu | $R^1$ | n-Bu |
| | $R^2$ | n-Bu | $R^2$ | n-Bu |
| Triisopropylphosphite | $R^1$ | i-Pr | $R^1$ | i-Pr |
| | $R^2$ | i-Pr | $R^2$ | i-Pr |
| Trimethylphosphite | $R^1$ | CH$_3$ | $R^1$ | CH$_3$ |
| | $R^2$ | CH$_3$ | $R^2$ | CH$_3$ |
| Triphenylphosphite | $R^1$ | $C_6H_5$ | $R^1$ | $C_6H_5$ |
| | $R^2$ | $C_6H_5$ | $R^2$ | $C_6H_5$ |
| Triethylphosphite | $R^1$ | $C_2H_5$ | $R^1$ | $C_2H_5$ |
| | $R^2$ | $C_2H_5$ | $R^2$ | $C_2H_5$ |

We claim:

1. A compound having Formula V

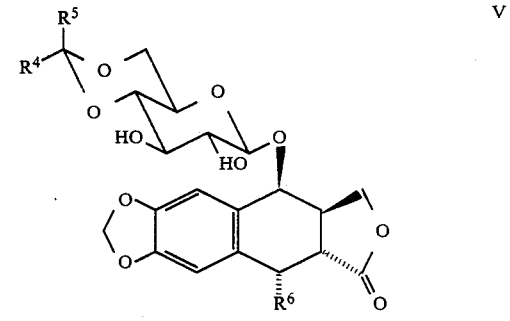

wherein $R^6$ is a structure selected from Formulas Va, Vb, Vc, and Vd

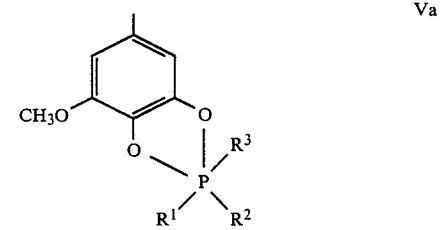

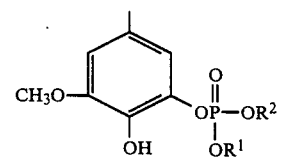

-continued

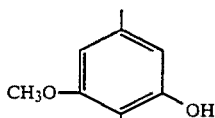
Vc

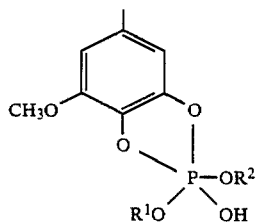
Vd wherein $R^1$, $R^2$, and $R^3$ are substituted or unsubstituted groups having a maximum of 20 carbon atoms and independently selected from the group consisting of alkyl or A-substituted alkyl having 1–12 carbon atoms, alkenyl or A-substituted alkenyl having 2–12 carbon atoms, cycloalkyl or A-substituted cycloalkyl having 3–7 ring carbon atoms, aryl or B-substituted aryl having 6–10 ring carbon atoms, and aralkyl or B-substituted aralkyl having 6–10 ring carbon atoms and 1–4 carbon atoms in the alkyl portion, wherein said A substituents are one or more groups selected from hydroxy, cyano, and halo, and said B substituents are selected from alkyl or a group listed in the A substituent definition, and $R^4$ and $R^5$ are each alkyl groups having 1–10 carbon atoms, or they are joined to form with the carbon atom to which they are attached a cycloalkyl group of 5 or 6 ring members, or one of them is hydrogen and the other is $C_{1-10}$alkyl, $C_{2-10}$alkenyl, $C_{4-7}$cycloalkyl, furyl, thienyl, $C_{6-10}$aryl, or $C_{7-14}$aralkyl.

2. The compound of claim 1 wherein $R^4$ is methyl, $R^5$ is hydrogen, and $R^6$ is a structure of Formula Va, and $R^1$, $R^2$, and $R^3$ are as defined in claim 1.

3. The compound of claim 2 wherein $R^1$, $R^2$, and $R^3$ are each ethyl.

4. The compound of claim 2 wherein $R^1$ is methyl and $R^2$ and $R^3$ are each hydroxymethyl.

5. The compound of claim 2 wherein $R^1$, $R^2$, and $R^3$ are each 2-cyanoethyl.

6. The compound of claim 1 wherein $R^4$ is methyl, $R^5$ is hydrogen, and $R^6$ is a structure selected from Formulas Vb, Vc, and Vd, and $R^1$, and $R^2$, are as defined in claim 1.

7. The compound of claim 6 wherein $R^1$ and $R^2$ are each 2-chloroethyl.

8. A composition comprising a mixture of equal parts by weight of two compounds of claim 1 wherein $R^4$ is methyl, $R^5$ is hydrogen, $R^6$ in one of said compounds is a structure of Formula Vb and in the other Formula Vc, and $R^1$ and $R^2$ are the same in each of said compounds and defined as in claim 1.

9. The composition of claim 8 wherein $R^1$ and $R^2$ are each 2-chloroethyl.

10. The compound of claim 1 wherein $R^5$ is H; $R^4$ is methyl; and $R^1$, $R^2$, and $R^3$ are independently selected from the group consisting of alkyl having 1–12 carbon atoms optionally substituted with one or more groups selected from halo, hydroxy, and cyano; cycloalkyl having 3–7 ring carbon atoms; and phenyl.

* * * * *